United States Patent [19]

Solem et al.

[11] Patent Number: 4,886,487

[45] Date of Patent: Dec. 12, 1989

[54] AUTOTRANSFUSION APPARATUS

[75] Inventors: Jan O. Solem, Bjarred; Olev Pilman, Lund, both of Sweden

[73] Assignee: Gambro AB, Sweden

[21] Appl. No.: 932,173

[22] Filed: Nov. 18, 1986

[30] Foreign Application Priority Data

Nov. 18, 1985 [SE] Sweden ................................ 8505438

[51] Int. Cl.$^4$ ............................................ A61M 37/00
[52] U.S. Cl. .......................................................... 604/5
[58] Field of Search ........................................ 604/4–6

[56] References Cited

U.S. PATENT DOCUMENTS

| | | | |
|---|---|---|---|
| 2,357,238 | 11/1943 | Trimble | 604/4 |
| 3,489,145 | 1/1970 | Judson et al. | |
| 3,896,733 | 7/1975 | Rosenberg | 604/4 |
| 3,965,896 | 6/1976 | Swank | |
| 4,006,745 | 2/1977 | Sorenson et al. | |
| 4,014,329 | 3/1977 | Welch et al. | |
| 4,033,345 | 7/1977 | Sorenson et al. | |
| 4,047,526 | 9/1977 | Reynolds et al. | |
| 4,146,172 | 3/1979 | Cullis et al. | |
| 4,185,629 | 1/1980 | Cullis et al. | |
| 4,187,979 | 2/1980 | Cullis et al. | |
| 4,216,770 | 8/1980 | Cullis et al. | |
| 4,379,452 | 4/1983 | Devries | 604/6 |
| 4,443,220 | 4/1984 | Haver et al. | 604/4 |
| 4,540,406 | 9/1985 | Miles | |
| 4,547,186 | 10/1985 | Bartlett | |
| 4,551,131 | 11/1985 | Miles et al. | |
| 4,622,032 | 11/1986 | Katsura et al. | 604/4 |
| 4,631,050 | 12/1986 | Reed et al. | 604/4 |
| 4,648,866 | 3/1987 | Malbrancq et al. | |
| 4,655,742 | 4/1987 | Vantard | |
| 4,657,529 | 4/1987 | Prince et al. | |
| 4,687,580 | 8/1987 | Malbrancq et al. | 604/6 |

FOREIGN PATENT DOCUMENTS

| 8400892 | 3/1984 | World Int. Prop. O. | 604/4 |
|---|---|---|---|
| 8402473 | 7/1984 | World Int. Prop. O. | 604/4 |

*Primary Examiner*—C. Fred Rosenbaum
*Assistant Examiner*—Mark F. Colosimo
*Attorney, Agent, or Firm*—Lerner, David, Littenberg, Krumholz & Mentlik

[57] ABSTRACT

Autotransfusion apparatus is disclosed for employing a patient's blood as a source for providing a transfusion, and which can also supply anticoagulant and diluting solution to the blood collected from a patient. The apparatus including a cardiotomy reservoir for collecting the patient's blood, a blood filter for separating a filtrate from the blood, a blood retention bag for retaining the treated blood and from which the blood can be returned to the patient by gravity.

19 Claims, 1 Drawing Sheet

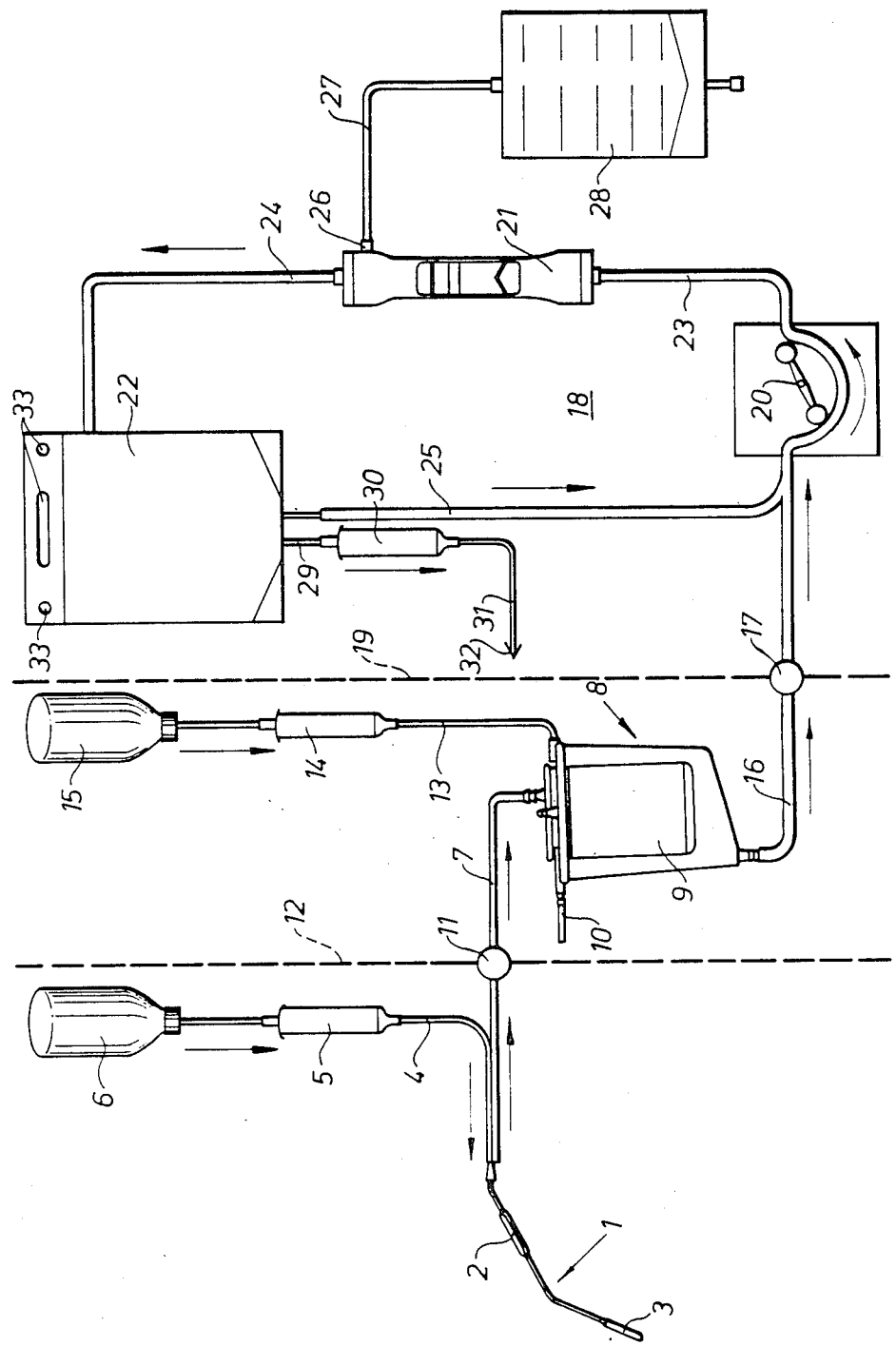

AUTOTRANSFUSION APPARATUS

FIELD OF THE INVENTION

The present invention relates generally to transform systems, and more particularly to an autotransfusion apparatus for employing a patient's blood as a source for providing a transfusion.

The apparatus is intended to be used per- and postoperatively, for example in intensive-care wards after major operations or for direct use during operations where major hemorrhages may occur, such as, in connection with vascular surgery, liver operations, orthopedic operations such as hip-joint operations, and the like.

BACKGROUND OF THE INVENTION

In the past, the apparatus which have been commercially available for effecting autotransfusion include those marketed under the name of Haemonetics Cell Saver, IBM Cell Washer and Dideco, all of which employ centrifuging apparatus. Thus, after a careful wash, these devices yield a final product containing only red blood cells in a salt solution. These apparatus are also relatively expensive, owing to the centrifuges included. An example of a system of this type can be found in the article "Autotransfusion and Emergency Surgery; Preliminary Report on an Improved Technique" in The International Journal of Artificial Organs, Vol. 8, No. 4, 1985, P. 221–224.

Simpler systems also exist, however, including those which are sold under the name of Sorenson and Solcotrans. These systems consist quite simply of a plastic canister which is prefilled with a certain amount of ACD-solution, and which is provided with a built-in filter. When the canister has thus been filled with blood it is simply turned upside down, so that the blood can be retransfused through the filter. These types of simplified systems, however, are not sufficiently effective in the case of more severe hemorrhages. Moreover, in view of the nature of these systems, the returned blood frequently also contains washing liquids, anticoagulants and other additives.

SUMMARY OF THE INVENTION

It is an object of the invention to provide a simple apparatus which can now render it possible to return wholly or partly cleaned whole blood, including its plasma as well as other valuable substances, such as coagulation factors and the like. It is also an important objective hereof to concentrate the whole blood to a suitable hematocrit value, by filtering off superfluous salt solution and anticoagulant solution.

In accordance with the present invention, these and other objects have now been realized by the discovery of autotransfusion apparatus for employing a patient's blood as a source for providing a transfusion which comprises collecting means for collecting the patient's blood; treatment means comprising filter means for filtering the collected blood so as to separate a filtrate from the blood and remove undesired portions thereof; a blood retention vessel for retaining the treated blood; and return means for returning the treated blood from the blood retention vessel to the patient.

In accordance with a preferred embodiment of the autotransfusion apparatus of the present invention, the filter means includes a blood inlet, a blood outlet, and a filtrate outlet; the blood retention vessel includes an inlet and an outlet; and the filter means and the blood retention vessel comprise a recirculation circuit including conduit means for connecting the blood outlet of the filter means to the inlet of the blood retention vessel and the outlet of the blood retention vessel to the blood inlet for the filter means. Preferably, the recirculation circuit further includes a peristaltic pump for recirculating the blood therein.

In accordance with another embodiment of the autotransfusion apparatus of the present invention, the apparatus further includes a filtrate receptacle coupled to the filtrate outlet so that filtrate can be collected without contact with the ambient atmosphere. Preferably, the blood retention vessel includes a blood return outlet, and the return means comprises a blood return conduit coupled to the blood return outlet, including control means for controlling the flow of the blood in the blood return conduit. The blood retention vessel can also preferably include suspension means for suspending the blood retention vessel so that blood may flow therefrom by means of gravity.

In accordance with a preferred embodiment of the autotransfusion apparatus of the present invention, the collecting means includes diluting means for supplying a diluting solution to the blood, and intermediate blood storage means for storing the blood. Preferably, the intermediate blood storage means comprises a cardiotomy reservoir including blood filter means. The diluting means is preferably connected to the intermediate blood storage means so that the diluting means can supply the diluting solution to the intermediate blood storage means.

In accordance with the embodiment of the autotransfusion apparatus of the present invention, the collecting means further includes suction means for drawing the patient's blood, and anticoagulant supply means for supplying anticoagulant to the patient's blood. The suction means preferably includes first duct means for connecting the suction means for transporting the blood drawn by the suction means, and second duct means for connecting to the anticoagulant supply means. The anticoagulant supply means preferably includes anticoagulant control means for controlling the supply of the anticoagulant, and the diluting means includes diluting solution control means for controlling the supply of the diluting solution. Further, the apparatus preferably comprises uncoupling means for uncoupling the collecting means from the treatment means.

By including the filter in a recirculation circuit comprising the peristaltic pump, it is possible to utilize a filter possessing a limited capacity, and which therefore can be relatively inexpensive, and thereby suitable for a single use. The peristaltic pump also facilitates utilization of the apparatus of the present invention; since, the pump is adapted to work on a conventional pump segment, whereby the pump does not come into direct contact with the blood. The collecting vessel of the present invention permits continuous treatment of the blood, and also continuous return of the blood, even when the blood is supplied intermittently to the apparatus. Further, the blood may be returned to the patient solely by means of gravity. By coupling the filter to a filtrate bag for collection of the filtrate without exposure to the ambient atmosphere, the risk of contamination is diminished. Thus, it is possible to use an expendable filter for a longer period then if it were connected to an open drain. The cardiotomy reservoir provided with a filter permits the treatment of blood to be deferred until the amount thereof collected is sufficient to warrant such activity.

BRIEF DESCRIPTION OF THE DRAWING

The sole figure is a schematic drawing of a preferred embodiment of the invention.

DETAILED DESCRIPTION

The preferred embodiment of the present invention shown in the sole figure comprises a suction device 1 with a hand-operated device 2 and a suction tip 3 which preferably is designed as a filter basket in order to prevent lumps or the like from being drawn up thereby. Although not shown in the drawings, the suction device 1 is preferably provided with two ducts, one of which is adapted to be used for drawing up the blood, whereas the other is adapted for the supply of an anticoagulant, which is supplied from a source 6 which can be a bottle containing ACD (Acid-Citrate-Dextrose) through duct 4 which includes a monitoring device 5. However, the means for collecting blood can be connected to a catheter for directly drawing of the blood from the site of the operation, particularly when used postoperatively. Monitoring device 5 controls the flow of anticoagulant, and may comprise a simple drip chamber. The blood drawn up by means of the suction device 1 passes through duct 7 to an intermediate storage vessel 8, which in the present embodiment preferably comprises a conventional cardiotomy reservoir provided with a filter 9 for filtering the blood. An intermediate storage vessel is particularly appropriate in the event of minor hemorrhages. With this vessel, treatment of the blood may be deferred until a sufficient amount of blood has been collected. In postoperative use it may be appropriate to prefill this intermediate storage vessel with diluent and/or anticoagulant. The cardiotomy reservoir 8 is connected via a duct 10 to a vacuum source, which is not shown in the drawing. The apparatus of the present invention can be divided by a coupling 11 into a suction part on the left side of the broken line 12, and a treatment part on the right side thereof. However, if the duct 7 is connected directly to a draw-off catheter connected to the site of the operation, such as in postoperative applications, the suction part of the apparatus is not required.

A duct 13 is connected to the cardiotomy reservoir 8 for conveying diluting fluid, such as a physiological salt solution from a source 15 for such a solution through a monitoring device 14. Monitoring device 14 controls the flow of the diluent, and may comprise a simple drip chamber. This solution is then mixed with the blood in reservoir 8. The salt solution protects the red blood corpuscles, provides a certain amount of washing, and can be removed with the help of a filter prior to return of the blood to a patient. Even without diluting fluid, the blood may have to be concentrated prior to return in order to remove excess anticoagulant or rinse fluid conveyed to the site of an operation. From the reservoir 8 the mixture is conducted through a duct 16 and a further coupling 17, which is shown schematically in the figure, to a recirculation circuit, which in its entirety is designated by reference numeral 18. The overall system can thus also be divided by means of coupling 17 along broken line 19, the parts to the left of which are intended primarily for collection and dilution of the blood, whereas the parts to the right of same are intended for concentration and return of the blood to the patient. Coupling 17 facilitates the assembly and disassembly of the apparatus downstream of the intermediate storage vessel. In this fashion, the apparatus can be divided into two expendable portions, one comprising the intermediate storage vessel and elements arranged upstream therefrom, and the other comprising elements downstream therefrom. In recirculation circuit 18 the blood is pumped by means of a peristaltic pump 20 through a filter 21 to a collecting vessel 22. Since the filter 21 is included in the recirculation circuit 18 which also comprises the pump 20, it is possible to select a filter which has a limited capacity and which, therefore, can be relatively inexpensive, so that it can be used only once. The peristaltic pump also facilitates treatment involving only a single use, since the pump can be adapted to work on a conventional pump segment without making direct contact with the blood. This is accomplished by means of ducts 23 and 24 and shunt duct 25. The collecting vessel permits continuous treatment of the blood and continuous return of the blood, even if blood is supplied only intermittently to the apparatus. The outlet 26 for the filtrate is connected through duct 27 to a flexible filtrate bag 28 for the collection of the filtrate without exposure to the surrounding atmosphere. Accordingly, the risk of contamination is diminished. It is therefore possible to use an expendable filter for a longer period of time than would be possible if it were connected to an open drain. When treatment of the blood is finished, that is to say when the appropriate hematocrit value has been attained, the blood is then passed through duct 29, with a monitoring device 30, to a retransfusion duct 31, whose tip 32 is intended to symbolize an injection cannula. The monitoring device 30 controls the flow of retransfusion blood, and may comprise a simple drip chamber. Collecting vessel 22 is provided with means for its suspension. These means have been designated in the Figure by reference numeral 33, and in the example shown consist of a handle and two suspension eyes. In this fashion, the blood can be returned to the patient solely by means of gravity. Filter 21 comprises a filter of the type normally used for hemofiltration. If a more rapid concentration is desired, as in connection with the continuing treatment of a patient where there is a risk of heavy bleeding, it is possible to use a filter of the type normally used for plasmapheresis. Examples of membrane material intended for hemofiltration are found, for example, in EP 0 046 816 and EP 0 098 392. Similarly, examples of membranes suitable for use in plasmapheresis are found in EP 0 044 958 and EP 0 095554.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

We claim:
1. An autotransfusion apparatus for employing a patient's blood as a source for providing a transfusion, comprising:
   collecting means for collecting said patient's blood;
   treatment means for treating blood collected in said collection means, said treatment means comprising a blood recirculation circuit coupled to said collecting means for receiving blood from said collect- ing means and conducting blood through said recirculation circuit, said recirculation circuit including filter means for filtering blood being conducted therethrough so as to separate a filtrate from said blood and remove undesired portions thereof and a blood retention vessel for receiving blood treated in said filter means, said filter means including a blood inlet, a blood outlet, and a filtrate outlet, and said blood retention vessel including an inlet and an outlet, and said recirculation circuit further including conduit means connecting said blood outlet of said filter means to said inlet of said retention vessel and connecting said outlet of said blood retention vessel to said blood inlet of said filter means so that blood in said blood retention vessel may be conducted through said filter means for further treatment and then returned to said blood retention vessel; and return means separate from said collecting means and coupled to said blood retention vessel for returning blood from said blood retention vessel to said patient, so that said apparatus is capable of functioning continuously to withdraw, filter and return said patient's blood.

2. The autotransfusion apparatus of claim 1, wherein said filter means comprises a semipermeable membrane.

3. The autotransfusion apparatus of claim 1, wherein said recirculation circuit includes a peristaltic pump for recirculating said blood therein.

4. The autotransfusion apparatus of claim 1, including a filtrate receptacle coupled to said filtrate outlet so that filtrate can be collected without contact with an ambient atmosphere.

5. The autotransfusion apparatus of claim 1, wherein said blood retention vessel includes a blood return outlet, and wherein said return means comprises a blood return conduit coupled to said blood return outlet, and including control means for controlling the flow of said blood in said blood return conduit.

6. The autotransfusion apparatus of claim 1, wherein said blood retention vessel includes suspension means for suspending said blood retention vessel so that blood may flow therefrom by means of gravity.

7. The autotransfusion apparatus of claim 1, wherein said collecting means includes diluting means for supplying a diluting solution to said blood.

8. The autotransfusion apparatus of claim 7, wherein said collecting means includes intermediate blood storage means for storing said blood.

9. The autotransfusion apparatus of claim 8, wherein said intermediate blood storage means comprises a cardiotomy reservoir including blood filter means.

10. The autotransfusion apparatus of claim 8, wherein said diluting means is connected to said intermediate blood storage means whereby said diluting means can supply said diluting solution to said intermediate blood storage means.

11. The autotransfusion apparatus of claim 1 wherein said collecting means includes suction means for drawing said patient's blood.

12. The autotransfusion apparatus of claim 11, wherein said collecting means further comprises anticoagulant supply means for supplying anticoagulant to said patient's blood.

13. The autotransfusion apparatus of claim 12 wherein said suction means includes first duct means for connection to said suction means for transporting said blood drawn by said suction means and second duct means for connection to said anticoagulant supply means.

14. The autotransfusion apparatus of claim 13, wherein said collecting means includes diluting means for supplying a diluting solution to said blood.

15. The autotransfusion apparatus of claim 14, wherein said collecting means includes intermediate blood storage means for storing said blood.

16. The autotransfusion apparatus of claim 15, wherein said diluting means is connected to said intermediate blood storage means whereby said diluting means can supply said diluting solution to said intermediate blood storage means.

17. The autotransfusion apparatus of claim 12, wherein said anticoagulant supply means includes anticoagulant control means for controlling the supply of said anticoagulant thereby.

18. The autotransfusion apparatus of claim 7 wherein said diluting means includes diluting solution control means for controlling the supply of said diluting solution thereby.

19. The autotransfusion apparatus of claim 1, including uncoupling means for uncoupling said collecting means from said treatment means.

* * * * *